United States Patent
Campbell et al.

(10) Patent No.: US 10,081,706 B2
(45) Date of Patent: Sep. 25, 2018

(54) SIDE-CHAIN-FUNCTIONALIZED POLYHYDROXYALKANOATE MATERIALS

(71) Applicant: International Business Machines Corporation, Armonk, NY (US)

(72) Inventors: Eric J. Campbell, Rochester, MN (US); Sarah K. Czaplewski, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/397,016

(22) Filed: Jan. 3, 2017

(65) Prior Publication Data
US 2018/0186928 A1 Jul. 5, 2018

(51) Int. Cl.
| | | |
|---|---|---|
| *C12P 7/62* | (2006.01) | |
| *C12P 11/00* | (2006.01) | |
| *C12P 17/00* | (2006.01) | |
| *C08G 63/91* | (2006.01) | |
| *C08L 67/04* | (2006.01) | |

(52) U.S. Cl.
CPC ............ *C08G 63/912* (2013.01); *C12P 7/625* (2013.01)

(58) Field of Classification Search
CPC ... C12P 7/625; C12P 7/62; C12P 11/00; C12P 17/00
See application file for complete search history.

(56) References Cited

U.S. PATENT DOCUMENTS

| | | |
|---|---|---|
| 5,395,919 A | 3/1995 | Lee et al. |
| 6,495,152 B2 | 12/2002 | Steinbuchel et al. |
| 6,821,612 B1 | 11/2004 | Melik et al. |
| 6,828,357 B1 | 12/2004 | Martin et al. |

(Continued)

FOREIGN PATENT DOCUMENTS

| | | |
|---|---|---|
| WO | WO-1989/000202 A2 | 1/1989 |
| WO | WO-1995/020621 A1 | 8/1995 |

OTHER PUBLICATIONS

Dan Kai et al "Polyhydroxyalkanoates: Chemical Modifications Toward Biomedical Applications" ACS, 2013.*

(Continued)

*Primary Examiner* — Ling-Siu Choi
*Assistant Examiner* — Gennadiy Mesh
(74) *Attorney, Agent, or Firm* — Roy R. Salvagio; Robert R. Williams; Kennedy Lenart Spraggins LLP

(57) ABSTRACT

A process of forming a side-chain-functionalized polyhydroxyalkanoate (PHA) material is disclosed. The process includes forming a PHA material having a vinyl-terminated side-chain from a vinyl-terminated fatty acid via a bacterial fermentation process. The process also includes forming a PHA material having a hydroxyl-terminated side-chain from the PHA material having the vinyl-terminated side-chain. The process further includes chemically reacting the PHA material having the hydroxyl-terminated side-chain with 1,4-phenylenedimethanethiol or a chlorocoumarin or 2-furoyl chloride to form a side-chain-functionalized PHA material having a side-chain with a terminal cross-linkable group (e.g., thiol, coumarin, or furoyl group).

4 Claims, 10 Drawing Sheets

(56) References Cited

U.S. PATENT DOCUMENTS

| | | | |
|---|---|---|---|
| 6,908,720 | B2 | 6/2005 | Kenmoku et al. |
| 8,168,550 | B2 | 5/2012 | Collias et al. |
| 8,771,720 | B2 | 7/2014 | Williams et al. |
| 9,023,972 | B2 | 5/2015 | Chu et al. |
| 9,474,830 | B2 | 10/2016 | Seliktar et al. |
| 9,475,930 | B2 | 10/2016 | Weinlein et al. |
| 2001/0009769 | A1* | 7/2001 | Williams ............ A61K 47/482 435/135 |
| 2002/0028857 | A1 | 3/2002 | Holy |
| 2006/0147412 | A1* | 7/2006 | Hossainy ............ C08B 37/0072 424/78.27 |
| 2015/0290344 | A1 | 10/2015 | Alexis et al. |

OTHER PUBLICATIONS

Levine et al "Use of thiol-ene click chemistry to modify mechanical and thermalproperties of polyhydroxyalkanoates (PHAs)", Nov. 2015.*

Gumel et al "Modification of PHAs", Chapter 7,RSC Green Chemistry, Jan. 2015.*

Kim et al Poly-3-hydroxyalkanoates Containing Unsaturated Repeating Units Produced by Pseudomonas oleovorans Polym.Chem.vol. 33,1367-1374 (1995).*

Appendix P; List of IBM Patents or Applications Treated as Related, Jul. 13, 2017, 2 pages.

Roy et al., *Modification of Polyhydroxyalkanoates (PHAs)*, Chapter 7 of, "Polyhydroxyalkanoate (PHA) based Blends, Composites and Nanocomposites", Nov. 2014, pp. 149-150, Royal Society of Chemistry, London, UK.

Reich, *Sulfoxide and Selenoxide syn-Eliminations*, Advanced Organic Chemistry Course, Fall 2013, 5 pages, University of Wisconsin, Madison, [accessed Sep. 7, 2016], URL: www.chem.wisc.edu/areas/reich/chem547/2-redox%7B19%7D.htm.

Dupont, *DuPont Industrial Biosciences and ADM Announce Breakthrough Platform Technology for Long Sought-After Molecule*, Jan. 2016, 7 pages, DuPont.com (online), Wilmington, DE, URL: www.dupont.com/products-andservices/industrial-biotechnology/press-releases/dupont-adm-announce-platform-technology-for-long-sought-aftermolecule.html.

Gomez et al., "Figure 1", from, "Chapter 3: Making Green Polymers Even Greener: Towards Sustainable Production of Polyhydroxyalkanoates from Agroindustrial By-Products", of, "Advances in Applied Biotechnology", Edited by Marian Petre, Jan. 2012, p. 43, InTechOpen.com (online), URL: intechopen.com/books/advances-in-appliedbiotechnology/making-green-polymers-even-greener-towards-sustainable-production-of-polyhydroxyalkanoates-fromagro. . .

Lakshmi et al., *Reactivity Studies of Maleimide Epoxy Resin With Long Chained Amines*, Journal of the Chilean Chemical Society, vol. 56, No. 3, 2011, pp. 725-728, Scientific Electronic Library Online (SciELO) Chile, URL: http://www.scielo.cl/scielo.php?pid=S0717-97072011000300001&script=sci_arttext.

* cited by examiner

US 10,081,706 B2

SIDE-CHAIN-FUNCTIONALIZED POLYHYDROXYALKANOATE MATERIALS

BACKGROUND

Plastics are typically derived from a finite and dwindling supply of petrochemicals, resulting in price fluctuations and supply chain instability. Replacing non-renewable petroleum-based polymers with polymers derived from renewable resources may be desirable. However, there may be limited alternatives to petroleum-based polymers in certain contexts. To illustrate, particular plastics performance standards may be specified by a standards body or by a regulatory agency. In some cases, alternatives to petroleum-based polymers may be limited as a result of challenges associated with satisfying particular plastics performance standards.

SUMMARY

According to an embodiment, a process of forming a side-chain-functionalized polyhydroxyalkanoate (PHA) material is disclosed. The process includes forming a PHA material having a hydroxyl-terminated side-chain. The process also includes utilizing the PHA material having the hydroxyl-terminated side-chain to form the side-chain-functionalized PHA material. The side-chain-functionalized PHA material includes a side-chain with a terminal cross-linkable functional group.

According to another embodiment, a process of forming a side-chain-functionalized PHA material is disclosed. The process includes forming a PHA material having a vinyl-terminated side-chain via a bacterial fermentation process. The process also includes forming a PHA material having a hydroxyl-terminated side-chain from the PHA material having the vinyl-terminated side-chain. The process further includes utilizing the PHA material having the hydroxyl-terminated side-chain to form the side-chain-functionalized PHA material. The side-chain-functionalized PHA material has a side-chain with a terminal cross-linkable functional group.

According to another embodiment, a process of forming a reversibly cross-linked PHA material is disclosed. The process includes forming a side-chain-functionalized PHA material from a PHA material having a hydroxyl-terminated side-chain. The side-chain-functionalized PHA material has a side-chain with a terminal cross-linkable functional group. The process also includes initiating a reversible chemical reaction between a first cross-linkable functional group of a first side-chain-functionalized PHA material and a second cross-linkable functional group of a second side-chain-functionalized PHA material to form a reversibly cross-linked PHA material.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes side-chain-functionalized PHA materials and methods of forming side-chain-functionalized PHA materials. After forming a PHA material having a hydroxyl-terminated side-chain, the PHA material having the hydroxyl-terminated side-chain may be utilized to form a functionalized PHA material having a side-chain with a terminal functional group. The terminal functional group may enable cross-linking and/or reversibly bonding of one side-chain-functionalized PHA material to a polymer backbone of another side-chain-functionalized PHA material.

As used herein, the term "PHA material" is used to refer to a poly(3-hydroxyalkanoate) material, which is a group of storage polymers produced by many types of bacteria in response to growth restriction by a nutrient other than the carbon source. To illustrate, *Pseudomonas oleovorans* is an example of a microorganism that produces PHAs with relatively long pendant side-chains. The long side-chains may contain some functionalities, such as olefins, that may provide sites for chemical modifications. Other suitable bacteria may be utilized in other cases.

The mechanical properties of the polymer can be tuned by varying the chain length of the aliphatic fatty acid(s) used in forming the PHAs or by varying the length of the PHAs themselves, which may be achieved by modifying reaction conditions, such as time, temperature, and the bacteria chosen for fermentation. In some cases, the PHA materials of the present disclosure may be utilized as stand-alone polymers or may be blended with other plastics (e.g., those derived from non-renewable sources) for varying applications. Illustrative examples of plastics for blending include polylactic acid, polyurethanes, polycarbonates, acrylonitrile butadiene styrene (ABS), polyesters, polyethers, or combinations thereof, among other alternatives. The appropriate blend ratio may vary in order to achieve a desired combination of mechanical properties.

Figure 1:
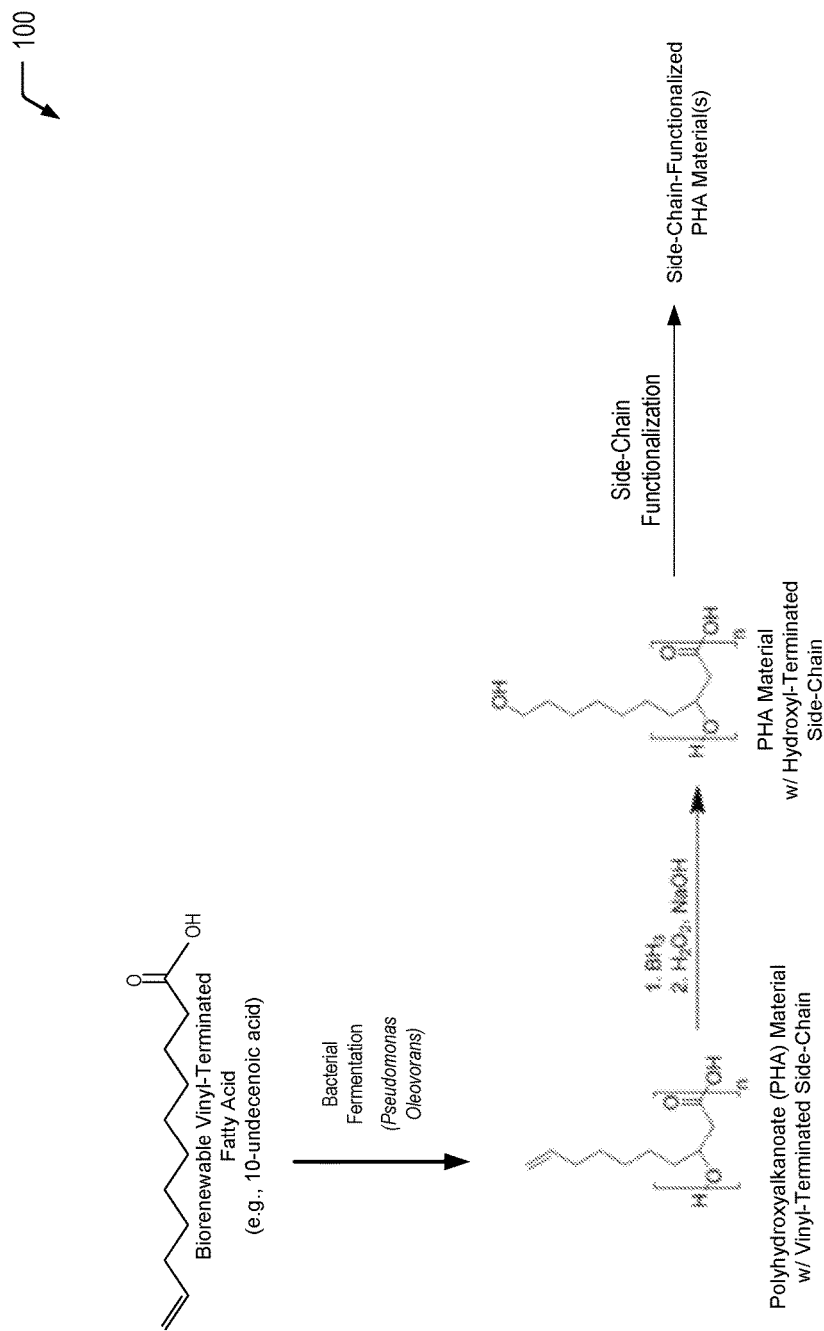
FIG. 1 is a chemical reaction diagram illustrating a process of forming a PHA material having a hydroxyl-terminated side-chain for subsequent side-chain functionalization, according to one embodiment.

Referring to FIG. 1, a chemical reaction diagram 100 illustrates an example of a process of forming a PHA material having a hydroxyl-terminated side-chain for subsequent side-chain functionalization, according to one embodiment. As described further herein, the PHA material having the hydroxyl-terminated side-chain depicted in FIG. 1 may be utilized to form various functionalized PHA materials having side-chains with terminal functional groups. As illustrated and further described herein with respect to FIGS. 2A-2C, 4, 6 and 7, the functional groups may include a thio group, a coumarin group, a diene group, or a dienophile group (among other alternative moieties or combinations of moieties). As illustrated and further described herein with respect to FIGS. 3, 5, and 8, the functional group(s) enable the formation of a reversibly cross-linked PHA material via a reversible chemical reaction, including a disulfide formation reaction, a coumarin photodimerization reaction, or a Diels-Alder reaction.

The first chemical reaction depicted in FIG. 1 illustrates the formation of a PHA material having a vinyl-terminated side-chain from a vinyl-terminated fatty acid via a bacterial fermentation process. In the example of FIG. 1, a single biorenewable vinyl-terminated fatty acid is illustrated. In alternative embodiments, alternative and/or additional vinyl-terminated fatty acids may be utilized. In the particular embodiment illustrated in FIG. 1, the biorenewable vinyl-terminated fatty acid includes 10-undecenoic acid. In some cases, the biorenewable vinyl-terminated fatty acid (or multiple biorenewable vinyl-terminated fatty acids) may be formed from one or more biorenewable plant oils (e.g., castor oil in the case of 10-undecenoic acid). Other examples of biorenewable plant oils include vegetable oils, soybean oil, linseed oil, etc. Thus, while FIG. 1 illustrates one example of a single vinyl-terminated fatty acid, alternative and/or additional biorenewable vinyl-terminated fatty acid(s) of varying chain length may be used. In some cases, one or more properties of the PHA material with the vinyl-terminated side-chain may be "tunable" via selection of biorenewable vinyl-terminated fatty acid(s) of varying chain length. To illustrate, chain length may affect properties such as glass transition temperature, melting temperature, and/or various materials characteristics (e.g., impact resistance, compression properties, etc.).

A bacterial fermentation process may be used to form the PHA material having the vinyl-terminated side-chain. In the example of FIG. 1, *pseudomonas oleovorans* is illustrated as a bacterium that may be used for the bacterial fermentation process. Other suitable bacteria may be utilized in other cases. To illustrate, *pseudomonas oleovorans* may be grown in the presence of the biorenewable vinyl-terminated fatty acid (e.g., 10-undecenoic acid in the example of FIG. 1), and the resulting polymer may be extracted from lyophilized cells using chloroform and precipitated with methanol.

The second chemical reaction depicted in FIG. 1 illustrates that a vinyl group of the vinyl-terminated side-chain of the PHA material may be converted to a hydroxyl group. In a particular embodiment (depicted as steps 1 and 2 in FIG. 1), the terminal vinyl group may be converted to a terminal hydroxyl group via hydroboration chemistry. For example, hydroxylation of the PHA material may be performed using borane or 9-borobicyclononane (9-BBN), which attaches only to least substituted vinyl carbon.

As a prophetic example of hydroboration of the vinyl-terminated side-chain, to a dried reaction vessel charged with "PHA," under an inert atmosphere (argon/nitrogen), a mixture of anhydrous chloroform/THF (e.g., a ratio of about 1:6 to give a PHA concentration of about 0.1 M, but this ratio could be flexible) may be added. The reaction may be cooled to about 0° C., and a solution of borane (or other applicable reagent such as 9-BBN, or disiamylborane ≥1 equivalents per vinyl group) in THF may be added, dropwise. The reaction mixture may be warmed to room temperature and stirred for about 12 hours at room temperature. The reaction mixture may then be cooled to about 10° C., and a solution of NaOH may be added (3.0 M, in excess), followed by an addition of hydrogen peroxide (30 weight percent, in excess). The reaction mixture may be cooled to about −25° C., and a small amount of methanol (approx. 3% by volume) may be added, and the reaction may be stirred for a minimum of 10 minutes. A solution of 3M NaOH, approx. 5% by volume (approx. 1.3 equivalents), may then be added to the reaction mixture and may be stirred for about 15 minutes. A solution of hydrogen peroxide may then be added (approx. 30% in water, 3.5-4.0 equivalents). The reaction may be stirred at about −25° C. for about 1 hour, followed by a slow warming to about 40° C. over a time period of about 1 hour, followed by cooling to room temperature. The resulting solution may be filtered, and 1M HCl may be added dropwise until the reaction mixture reaches a neutral pH. The solvents may be removed in vacuo until a small amount remains, and the crude reaction mixture may be extracted with DMF, filtered, and the solvent removed in vacuo.

Figure 2A:
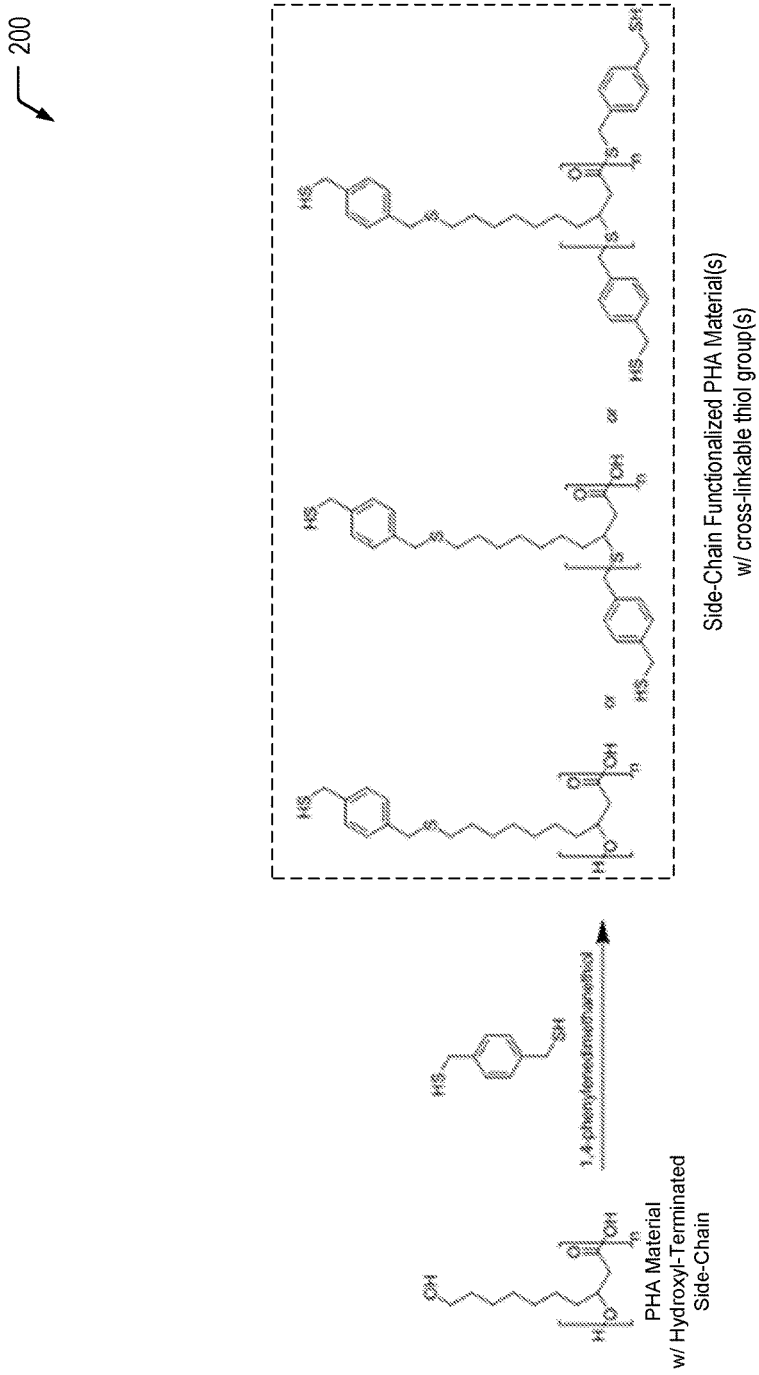
FIG. 2A is a chemical reaction diagram illustrating a process of forming a side-chain-functionalized PHA material having a side-chain with terminal thiol group(s), according to one embodiment.
Figure 4:
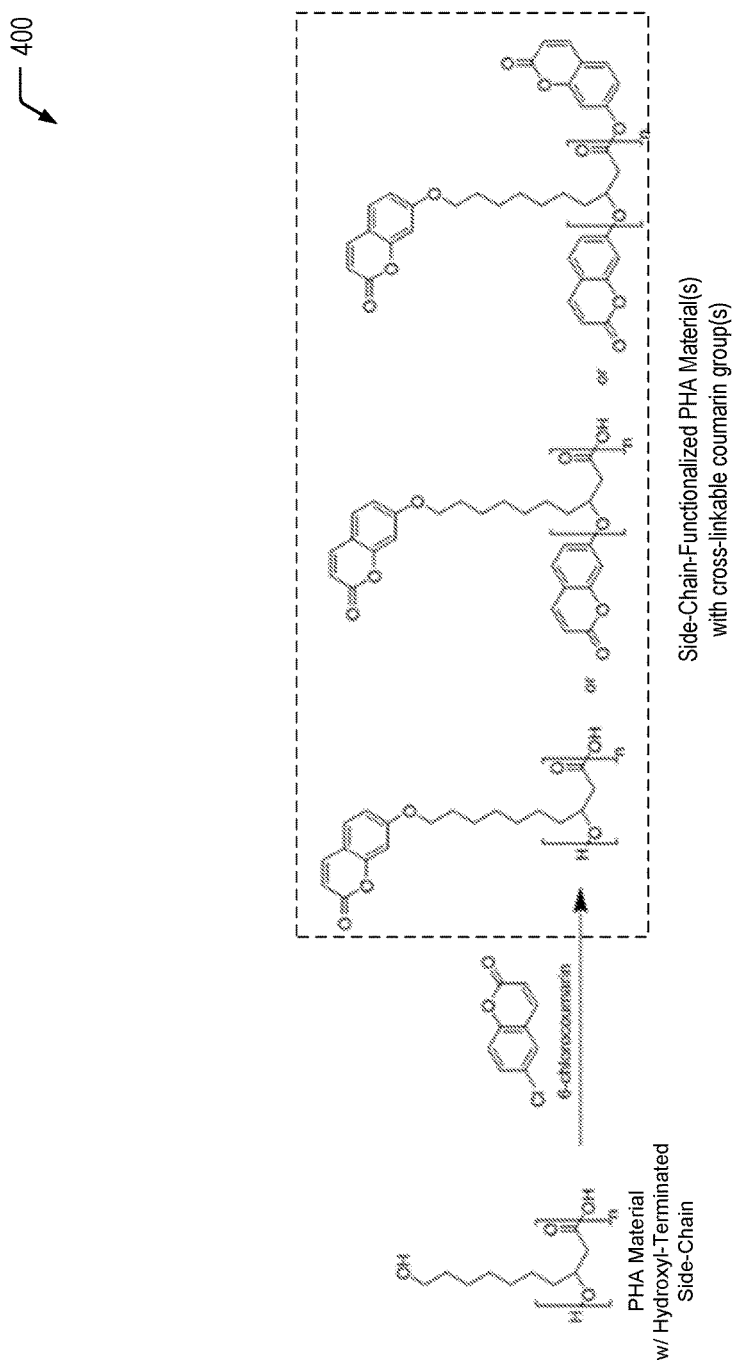
FIG. 4 is a chemical reaction diagram illustrating a process of utilizing the PHA material having the hydroxyl-terminated side-chain depicted in FIG. 1 to form a side-chain-functionalized PHA material having a side-chain with a terminal coumarin group, according to one embodiment.
Figure 6:
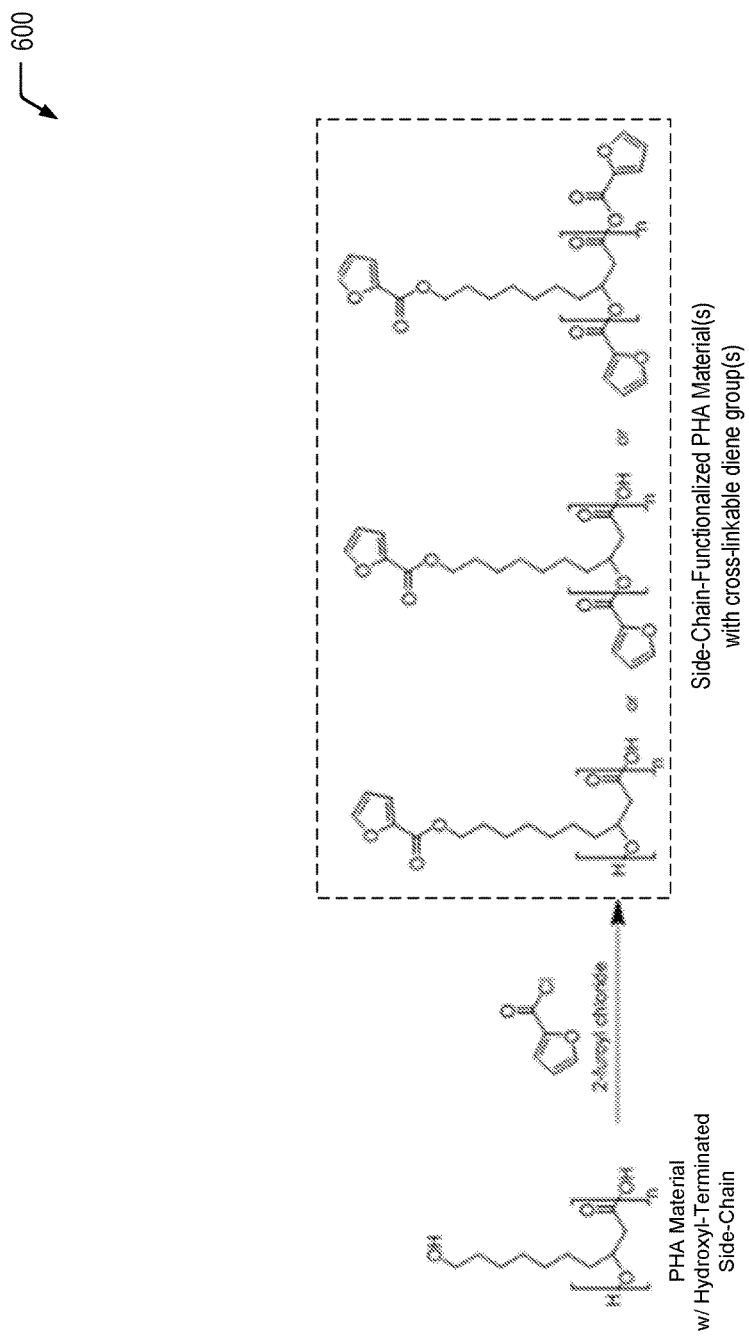
FIG. 6 is a chemical reaction diagram illustrating a process of utilizing the PHA material having the hydroxyl-terminated side-chain depicted in FIG. 1 to form a side-chain-functionalized PHA material having a side-chain with a terminal diene group, according to one embodiment.
Figure 7:
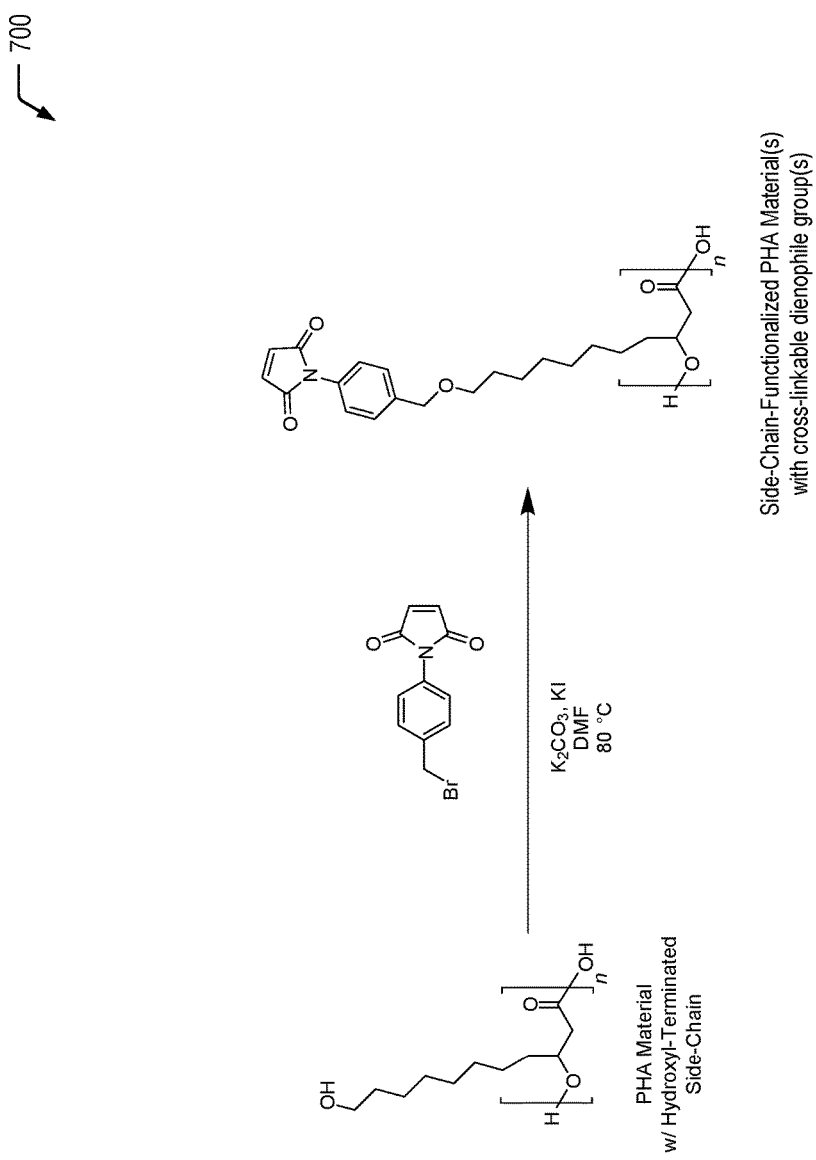
FIG. 7 is a chemical reaction diagram illustrating a process of utilizing the PHA material having the hydroxyl-terminated side-chain depicted in FIG. 1 to form a side-chain-functionalized PHA material having a side-chain with a terminal dienophile group, according to one embodiment.
Figure 8:
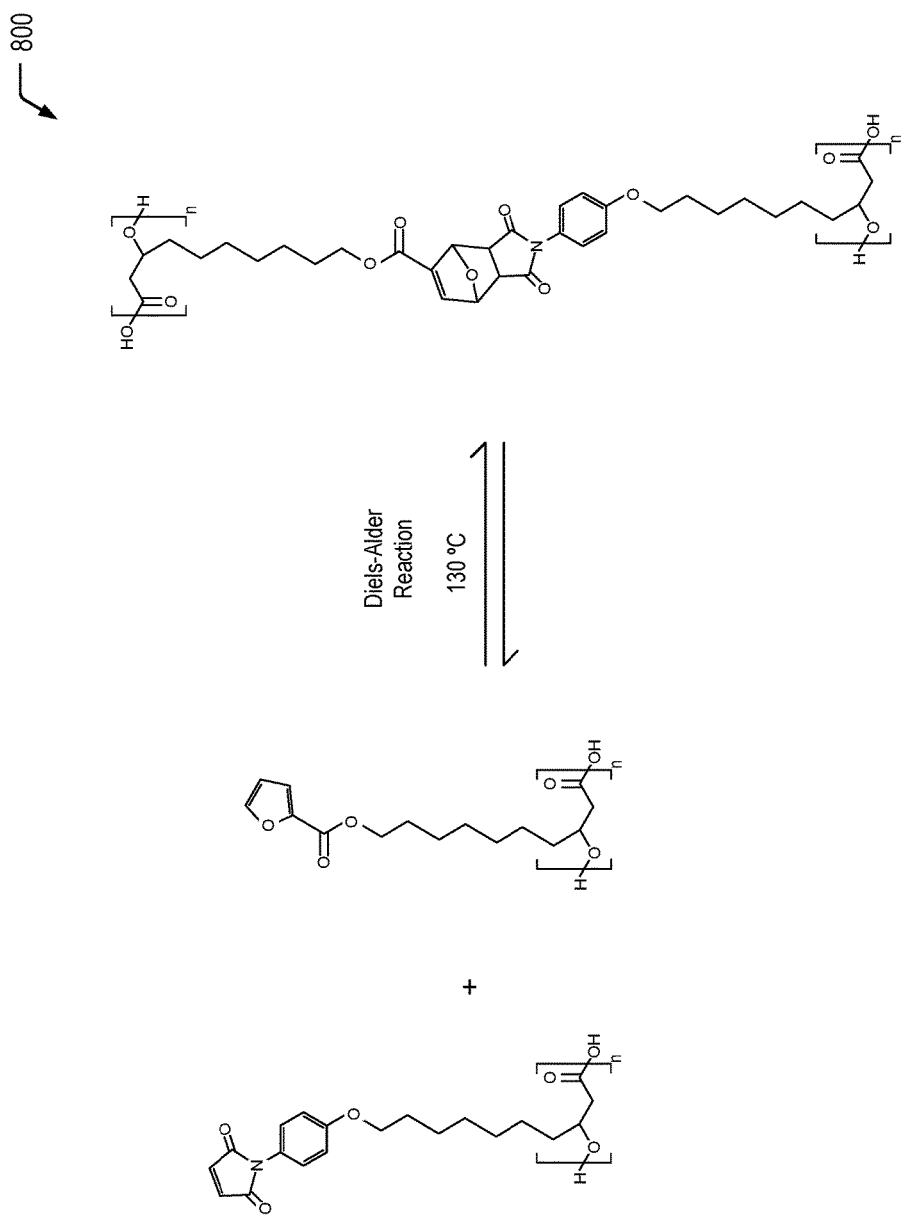
FIG. 8 is a chemical reaction diagram illustrating a process of utilizing the side-chain-functionalized PHA materials depicted in FIGS. 6 and 7 to form a reversibly cross-linked PHA material, according to one embodiment.

The third chemical reaction depicted in FIG. 1 illustrates that the PHA material with the terminal side-chain hydroxyl group may subsequently be utilized to form one or more side-chain-functionalized PHA materials, as further described herein. For example, FIG. 2A illustrates examples of side-chain-functionalized PHA materials including a side-chain with a terminal thiol group (and optionally one or more terminal thiol groups on the PHA backbone). As another example, FIG. 4 illustrates examples of side-chain-functionalized PHA materials including a side-chain with a terminal coumarin group (and optionally one or more terminal coumarin groups on the PHA backbone). As a further example, FIG. 6 illustrates examples of side-chain-functionalized PHA materials including a side-chain with a terminal diene group (and optionally one or more terminal diene groups on the PHA backbone). As yet another example, FIG. 7 illustrates examples of side-chain-functionalized PHA materials including a side-chain with a terminal amine group (and optionally one or more terminal amine groups on the PHA backbone). FIG. 7 further illustrates that the terminal amine groups may subsequently be converted to terminal dienophile groups (for a Diels-Alder reaction with the side-chain-functionalized PHA material of FIG. 6, as illustrated in FIG. 8).

Thus, FIG. 1 illustrates an example of a process of forming a PHA material having a hydroxyl-terminated side-chain for subsequent side-chain functionalization. Biorenewable materials may be used to form the PHA materials for subsequent side-chain functionalization, and the sidechain-functionalized PHA materials (or blends that include the side-chain-functionalized PHA materials) may be used in various applications in order to increase a biorenewable content.

Referring to FIG. 2A, a chemical reaction diagram 200 illustrates an example of a process of utilizing the PHA material having the hydroxyl-terminated side-chain depicted in FIG. 1 to form a side-chain-functionalized PHA material containing terminal cross-linkable thiol group(s), according to one embodiment. As illustrated and further described herein with respect to FIG. 3, one or more of the thiol group(s) may be utilized to form disulfide linkage(s) to reversibly cross-link one side-chain-functionalized PHA material to another side-chain-functionalized PHA material.

FIG. 2A illustrates that the PHA material may be chemically reacted with a dithiol to form one or more side-chain-functionalized-functionalized PHA materials with terminal thiol groups. In the particular embodiment depicted in FIG. 2A, the dithiol includes 1,4-phenylenedimethanethiol. In other cases, alternative and/or additional dithiol materials may be utilized. As illustrated and described further herein with respect to FIG. 3, the terminal thiol groups of the side-chain-functionalized PHA material(s) of FIG. 2A may represent locations for (reversible) cross-linking via one or more disulfide formation reactions.

As a prophetic example, the reaction may require a catalyst system of Palladium, (SP-4-2)-dichloro[1,1'-[[(4R,5R)-2,2-dimethyl-1,3-dioxolane-4,5-diyl]bis(methylene)]bis[1,1-diphenylphosphine-κP]] and silver triflate, in methyl nitrate at 50° C. for 24 hours. The reaction conditions may utilize NaOH in DMF. In some cases, the reaction may have more than one methylene (CH2) groups between the thiol (or protected thiol or halide etc.). To illustrate, in addition to methanethiol, other examples include ethanethiol or propanethiol, among other alternatives. An alternative example of prophetic reaction conditions may include using 4-(chloroalkyl)-benzenemethanethiol, and SN2 conditions (base/polar aprotic solvent). Another alternative example of prophetic reaction conditions may include the use of 4-(mercaptoalkyl)benzoyl chloride, and an amine (pyridine, triethyl amine, etc.).

Figures 2B, 2C:
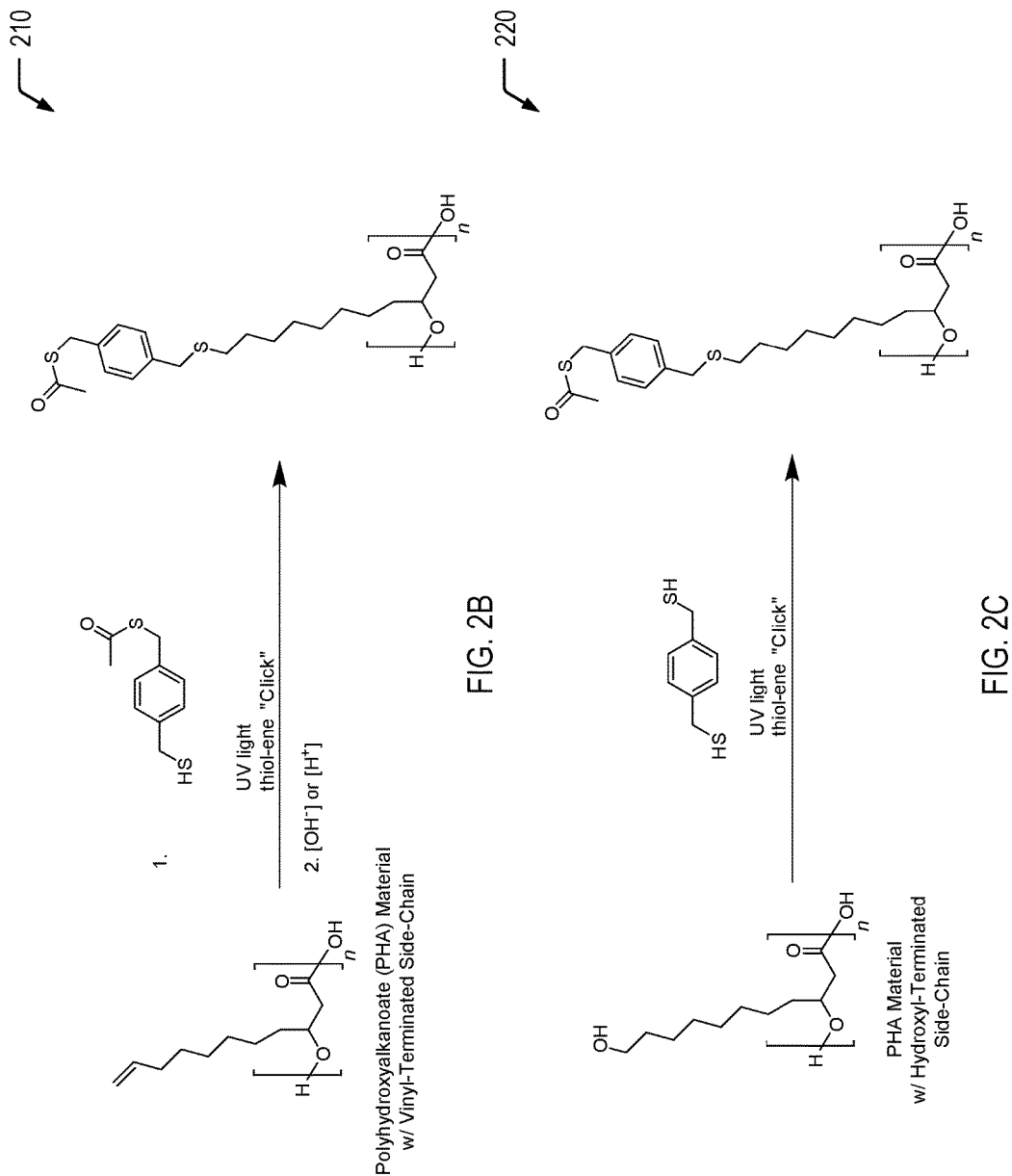
FIGS. 2B and 2C are chemical reaction diagrams illustrating alternative embodiments of processes of forming a side-chain-functionalized PHA material having a thio-terminated side-chain.

Thus, FIG. 2A illustrates an example of a process of utilizing the PHA material having the hydroxyl-terminated side-chain depicted in FIG. 1 to form a side-chain-functionalized PHA material containing terminal cross-linkable thiol group(s). As further described herein, the terminal thiol group(s) depicted in FIG. 2A may be utilized to form a PHA material that is reversibly cross-linked via disulfide linkage(s). FIGS. 2B and 2C depict alternative examples of processes of forming side-chain-functionalized PHA materials containing a terminal thio group.

Referring to FIG. 2B, a chemical reaction diagram 210 illustrates that, in some cases, a mono-protected thiol may be utilized (e.g., using a thioacetate, such as ethanethionic acid, S-[[4-(mercaptomethyl)phenyl]methyl] ester). The reaction should only include the hydroxyl groups, not the carboxylic acid terminal group. As a prophetic example, the reaction may require a sulfonyl chloride and make use of Zn/acetic acid reagents in ethyl acetate, followed by the addition of dichloromethylsilane.

Referring to FIG. 2C, a chemical reaction diagram 220 illustrates an alternative example in which the terminal thio group may be added via a thiol-ene "Click" reaction. FIG. 2C illustrates that the hydroxyl-terminated side-chain depicted in FIG. 1 may be chemically reacted with a dithiol. In the particular embodiment depicted in FIG. 2C, the dithiol includes 1,4-phenylenedimethanethiol. In other cases, alternative and/or additional dithiol materials may be utilized. As previously described herein with respect to FIG. 2B, the same mono-functionalized or mono-protected thiol reagents/rules may be appropriate. The thiol-ene reaction may utilize UV light and/or heat.

Figure 3:
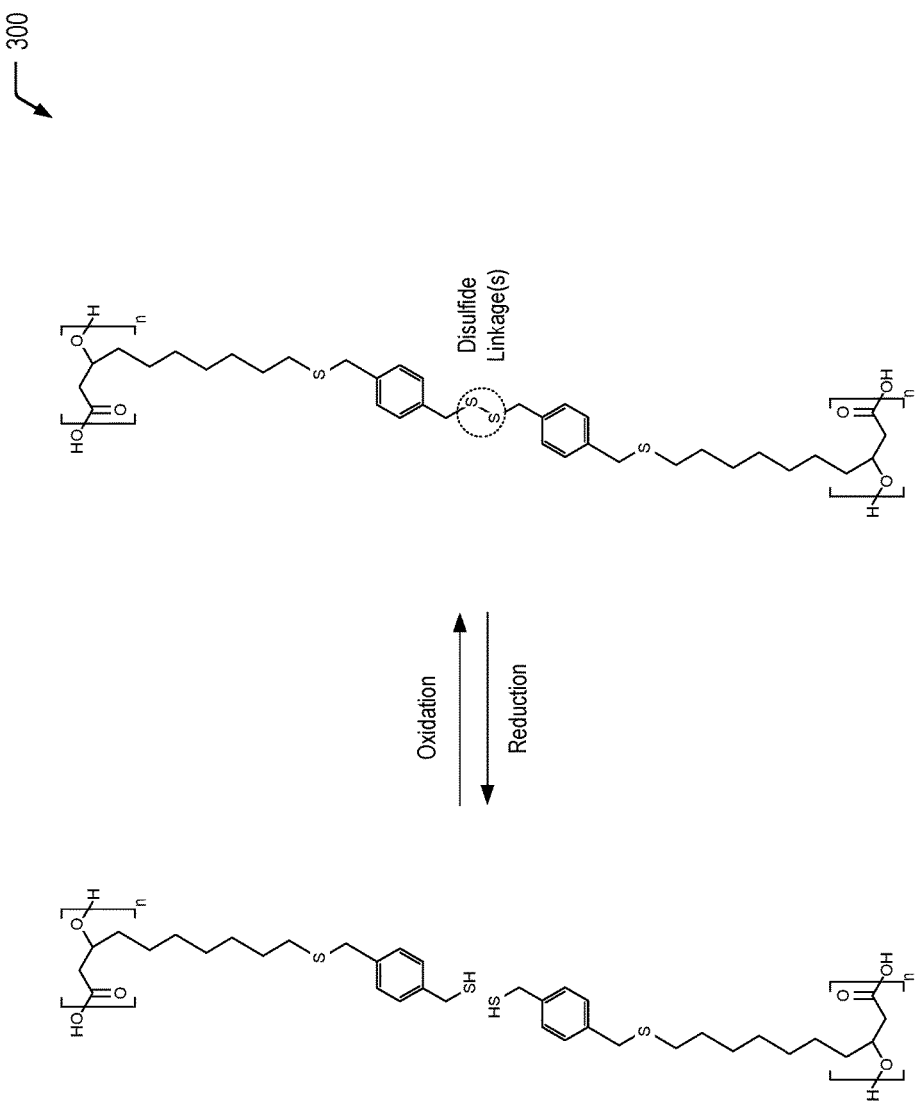
FIG. 3 is a chemical reaction diagram illustrating a process of utilizing one of the side-chain-functionalized PHA materials depicted in FIG. 2A to form a reversibly cross-linked PHA material, according to one embodiment.

Referring to FIG. 3, a chemical reaction diagram 300 illustrates an example of a process of utilizing one of the side-chain-functionalized PHA materials depicted in FIG. 2 to form a reversibly cross-linked PHA material. FIG. 3 illustrates that one or more of the thiol groups of the side-chain-functionalized PHA material(s) illustrated in FIG. 2A may chemically react to form disulfide group(s) that may reversibly cross-link one side-chain-functionalized PHA material to another side-chain-functionalized PHA material. For illustrative purposes only, the first example side-chain-functionalized PHA material depicted at the left of FIG. 2A is shown in FIG. 3. It will be appreciated that similar reactions may occur between the thiol group(s) depicted in the other example side-chain-functionalized PHA materials depicted in FIG. 2A to form disulfide linkage(s).

Referring to FIG. 4, a chemical reaction diagram 400 illustrates an example of a process of utilizing the PHA material having the hydroxyl-terminated side-chain depicted in FIG. 1 to form a side-chain-functionalized PHA material having a terminal coumarin group, according to one embodiment. As illustrated and further described herein with respect to FIG. 5, a reversibly cross-linked PHA material may be formed via a coumarin photodimerization reaction.

FIG. 4 illustrates that the PHA material having the hydroxyl-terminated side-chain may be chemically reacted with a coumarin material to form a side-chain-functionalized PHA material having a side-chain with a terminal coumarin group. In the particular embodiment depicted in FIG. 4, the coumarin material includes 6-chlorocoumarin. In other cases, alternative and/or additional coumarin materials may be utilized. As illustrated and described further herein with respect to FIG. 5, a coumarin photodimerization reaction may be utilized to form a reversibly cross-linked PHA material.

In a particular embodiment, the terminal hydroxyl group may be reacted with the coumarin material in solution or under melt conditions using an appropriate catalyst. As a prophetic example, Hydroxyl-functionalized PHA, cesium carbonate, and 6-chlorocoumarin (coumarin derivatives with chlorine groups at other positions may be used as well, resulting in the corresponded ether linked PHA-coumarin polymers), a catalytic (approx. 5%) palladium acetate, and a ligand such as Butyl-XPhos may be added to a dried reaction vessel under inert atmosphere. The two compounds may be dissolved in an organic solvent such as chloroform, THF, toluene, chlorobenzene, etc., and the reaction may be carried out at or above room temperature, under reflux conditions. Upon completion, the reaction may be cooled to room temperature, and the crude product may be dissolved in an organic solvent such as chloroform, THF, toluene, chlorobenzene etc., if no solvent was used to conduct the reaction. The polymer may be precipitated by pouring the solution into an organic non-polar solvent such as hexane, methanol, ethanol, acetone, etc. Any resulting solids may be filtered and purified further by techniques known to those skilled in the arts, such as Soxhlet extraction. Another possible synthetic route may use variably substituted hydroxycoumarins under Mistunobu conditions (triphenyl phosphine and an amine abbreviated DEAD, diethylazodicarboxylate).

Figure 5:
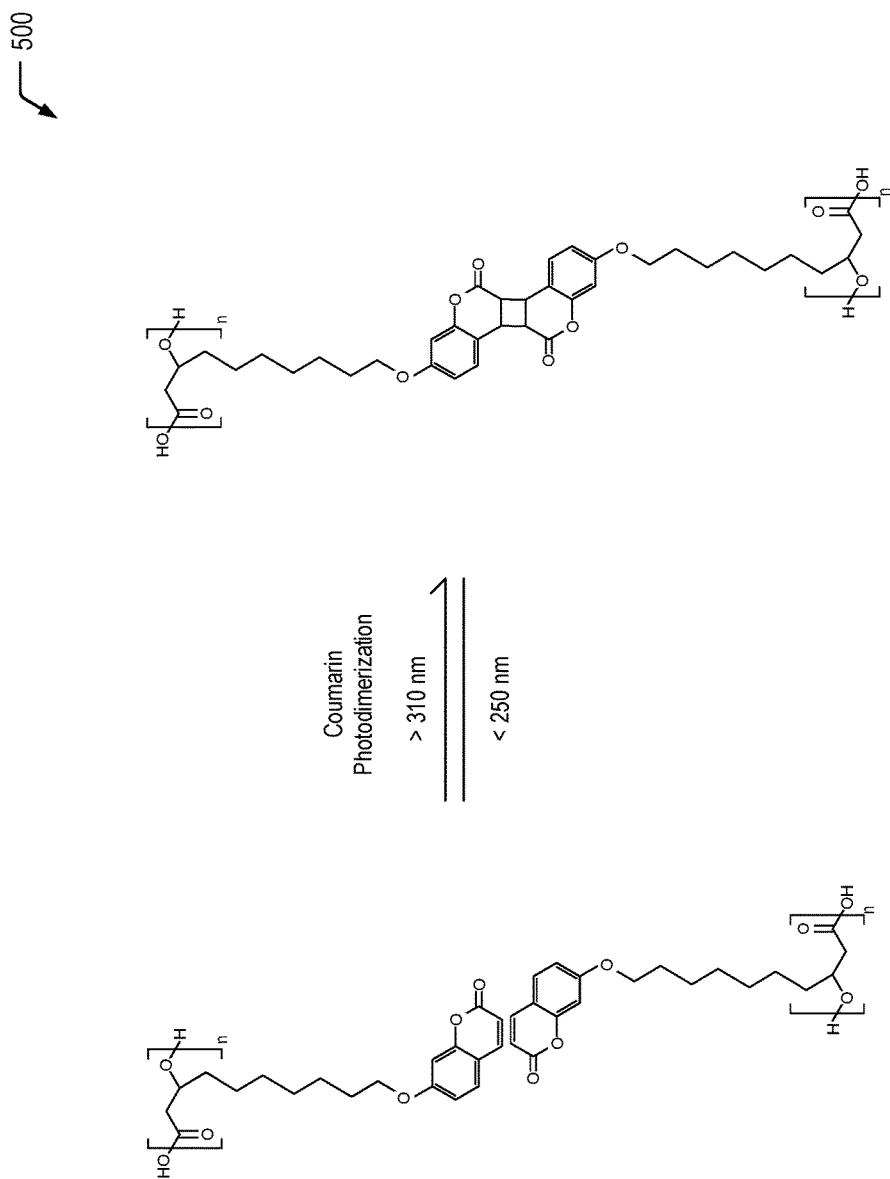
FIG. 5 is a chemical reaction diagram illustrating a process of utilizing the side-chain-functionalized PHA material depicted in FIG. 4 to form a reversibly cross-linked PHA material, according to one embodiment.

Referring to FIG. 5, a chemical reaction diagram 500 illustrates an example of a process of utilizing the side-chain-functionalized PHA material depicted in FIG. 4 to form a reversibly cross-linked PHA material via a coumarin photodimerization reaction. For example, exposure of the side-chain-functionalized PHA material depicted in FIG. 4 to UV light having a wavelength that is greater than 310 nm may result in the cross-linked PHA material depicted on the right side of FIG. 5. Exposure of the cross-linked PHA material depicted in FIG. 4 to UV light having a wavelength that is less than 250 nm may reverse the chemical reaction.

Referring to FIG. 6, a chemical reaction diagram 600 illustrates an example of a process of utilizing the PHA material having the hydroxyl-terminated side-chain depicted in FIG. 1 to form a side-chain-functionalized PHA material having a side-chain with a terminal diene group, according to one embodiment. In the particular embodiment depicted in FIG. 6, the diene material includes 2-furoyl chloride. In other cases, alternative and/or additional diene materials may be utilized. As illustrated and further described herein with respect to FIG. 8, a Diels-Alder reaction between the diene group of the side-chain-functionalized PHA material of FIG. 6 and the dienophile group of the side-chain-functionalized PHA material of FIG. 7 may enable the formation of a reversibly cross-linked PHA material.

In a particular embodiment, the terminal hydroxyl group may be reacted with the diene material in solution or under melt conditions using an appropriate catalyst. As a prophetic example, Hydroxyl-functionalized PHA and an amount of an amine such as triethyl amine, pyridine, or 4-(dimethylaminopyridine) (DMAP) (2 equiv.) may be added to a dried reaction vessel under inert atmosphere. The two compounds may be dissolved in an organic solvent such as chloroform, THF, toluene, chlorobenzene etc., and the reaction may be carried out at or above room temperature, under reflux conditions. A diene material (e.g., 2-furoyl chloride) may be added dropwise to the reaction mixture while stirring, at a temperature which may be 0° C. Upon completion, the reaction may be cooled to room temperature, and the crude product may be dissolved in an organic solvent such as chloroform, THF, toluene, chlorobenzene etc., if no solvent was used to conduct the reaction. The polymer may be precipitated by pouring the solution into an organic non-polar solvent such as hexane, methanol, ethanol, acetone, etc. Any resulting solids may be filtered and purified further by techniques known to those skilled in the arts, such as Soxhlet extraction.

Referring to FIG. 7, a chemical reaction diagram 700 illustrates an example of a process of utilizing the PHA material having the hydroxyl-terminated side-chain depicted in FIG. 1 to form a side-chain-functionalized PHA material having a side-chain with a terminal dienophile group, according to one embodiment. As illustrated and further described herein with respect to FIG. 8, a Diels-Alder reaction between the dienophile group of the side-chain-functionalized PHA material of FIG. 7 and the diene group of the side-chain-functionalized PHA material of FIG. 6 may enable the formation of a reversibly cross-linked PHA material.

As a prophetic example, the hydroxyl-functionalized PHA material, potassium carbonate, and a catalytic (approx. 5%) amount of potassium iodide may be added to a dried reaction vessel under inert atmosphere. The two compounds may be dissolved in an organic solvent such as chloroform, THF, DMF, chlorobenzene etc., and the reaction may be carried out at or above room temperature (e.g., 80° C.), under reflux conditions. A pyrrole-2,5-dione (e.g., 1-[4-(bromomethyl)phenyl]-1H-Pyrrole-2,5-dione, 1-(2-bromomethyl)-1H-Pyrrole-2,5-dione, or 1-(2-bromoethyl)-1H-Pyrrole-2,5-dione) may be added dropwise to the reaction mixture while stirring. Upon completion, the reaction may be cooled to room temperature, and the crude product may be dissolved in an organic solvent such as chloroform, THF, toluene, chlorobenzene etc., if no solvent was used to conduct the reaction. The polymer may be precipitated by pouring the solution into an organic non-polar solvent such as hexane, methanol, ethanol, acetone, etc. Any resulting solids may be filtered and purified further by techniques known to those skilled in the arts, such as Soxhlet extraction Thus, FIG. 7 illustrates an example of a process of utilizing the PHA material having the hydroxyl-terminated side-chain depicted in FIG. 1 to form a side-chain-functionalized PHA material having a side-chain with a terminal dienophile group. As illustrated and described further herein with respect to FIG. 8, a reversibly cross-linked PHA material may be formed via a Diels-Alder reaction between the dienophile group of the side-chain-functionalized PHA material of FIG. 7 and the diene group of the side-chain-functionalized PHA material of FIG. 6.

Referring to FIG. 8, a chemical reaction diagram 800 illustrates an example of a process of utilizing the side-chain-functionalized PHA materials depicted in FIGS. 6 and 7 to form a reversibly cross-linked PHA material via a Diels-Alder reaction. FIG. 8 illustrates that, at a temperature that is greater than 130° C., the PHA backbone of the side-chain-functionalized PHA material depicted in FIG. 6 may be coupled to the PHA backbone of the side-chain-functionalized PHA material depicted in FIG. 7. At a temperature that is less than 130° C., the reaction may be reversed.

Figure 9:
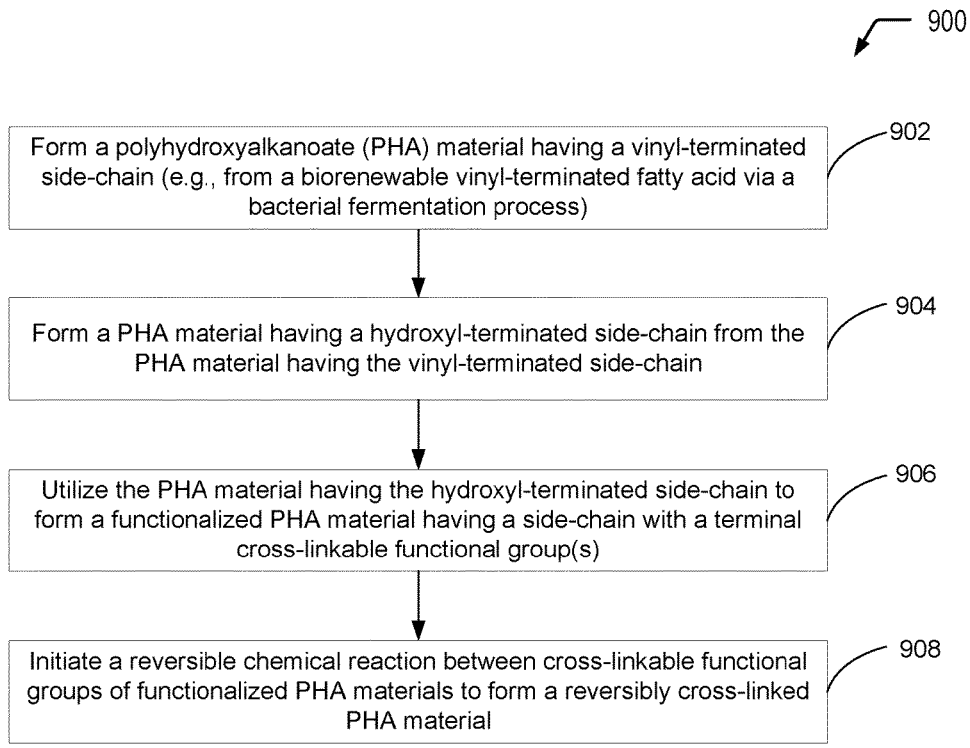
FIG. 9 is a flow diagram showing a particular embodiment of a process of utilizing a PHA material having a hydroxyl-terminated side-chain to form a side-chain-functionalized PHA material having a side-chain with a terminal cross-linkable functional group.

Referring to FIG. 9, a flow diagram illustrates a particular embodiment of a process 900 of utilizing a PHA material having a hydroxyl-terminated side-chain to form a side-chain-functionalized PHA material. In the particular embodiment depicted in FIG. 9, the process 900 also includes forming a reversibly cross-linked PHA material from the side-chain-functionalized PHA material. In the particular embodiment illustrated in FIG. 9, operations associated with an example process of forming a side-chain-functionalized PHA material having cross-linkable functional group(s) are identified as operations 902-904, while operations associated with utilizing the side-chain-functionalized PHA materials to form a reversibly cross-linked PHA material are identified as operation 906. It will be appreciated that the operations shown in FIG. 9 are for illustrative purposes only and that the operations may be performed in alternative orders, at alternative times, by a single entity or by multiple entities, or a combination thereof. As an example, one entity may form a PHA material with a vinyl-terminated side-chain (e.g., via a bacterial fermentation process), another entity may utilize the PHA material with the vinyl-terminated side-chain to form a PHA material with a hydroxyl-terminated side-chain, while another entity may utilize the PHA material with the hydroxyl-terminated side-chain to form the side-chain-functionalized PHA material, while yet another entity may utilize the side-chain-functionalized PHA materials to form the reversibly cross-linked PHA material.

The process 900 includes forming a PHA material having a vinyl-terminated side chain, at 902. For example, referring to the first chemical reaction depicted in FIG. 1, a bacterial fermentation process may be utilized to form the PHA material having the vinyl-terminated side chain from a vinyl-terminated fatty acid (e.g., a biorenewable vinyl-terminated fatty acid, such as 10-undecenoic acid).

The process 900 includes forming a PHA material having a hydroxyl-terminated side-chain from the PHA material having the vinyl-terminated side-chain, at 904. For example, referring to the second chemical reaction depicted in FIG. 1, the PHA material having the vinyl-terminated side-chain that is formed via the bacterial fermentation process may be utilized to form the PHA material having the hydroxyl-terminated side-chain.

The process 900 includes utilizing the PHA material having the hydroxyl-terminated side-chain to form a side-chain-functionalized PHA material having a side-chain with a terminal cross-linkable functional group, at 906. As an example, referring to FIG. 2A, the PHA material having the hydroxyl-terminated side chain depicted in FIG. 1 may be utilized to form a side-chain-functionalized PHA material having cross-linkable thiol group(s). As another example, referring to FIG. 4, the PHA material having the hydroxyl-terminated side chain depicted in FIG. 1 may be utilized to form a side-chain-functionalized PHA material having a side-chain with a terminal photodimerizable coumarin group. As a further example, referring to FIG. 6, the PHA material having the hydroxyl-terminated side chain depicted in FIG. 1 may be utilized to form a side-chain-functionalized PHA material having a side-chain with a terminal diene group. As yet another example, referring to FIG. 7, the PHA material having the hydroxyl-terminated side chain depicted in FIG. 1 may be utilized to form a side-chain-functionalized PHA material having a side-chain with a terminal dienophile group.

In the particular embodiment depicted in FIG. 9, the process 900 further includes initiating a reversible chemical reaction between cross-linkable functional groups of side-chain-functionalized PHA materials to form a reversibly cross-linked PHA material, at 908. As an example, in the embodiment depicted in FIG. 3, the reversible chemical reaction includes a disulfide formation reaction between the thiol group(s) of the side-chain-functionalized PHA material of FIG. 2A. As another example, in the embodiment depicted in FIG. 5, the reversible chemical reaction includes a coumarin photodimerization reaction. As yet another example, in the embodiment depicted in FIG. 8, the reversible chemical reaction includes a Diels-Alder reaction between the diene group of the side-chain-functionalized PHA material of FIG. 6 and the dienophile group of the side-chain-functionalized PHA material of FIG. 7.

Thus, FIG. 9 illustrates an example of a process of utilizing a PHA material having a hydroxyl-terminated side chain to form a side-chain-functionalized PHA material having cross-linkable functional group(s). In the case of thiol functional group(s), a reversibly cross-linked PHA material may be formed via a disulfide formation reaction. In the case of a coumarin group, a reversibly cross-linked PHA material may be formed via a coumarin photodimerization reaction. In the case of diene/dienophile functional groups, a reversibly cross-linked PHA material may be formed via a Diels-Alder reaction.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a side-chain-functionalized polyhydroxyalkanoate (PHA) material, the process comprising:
   forming a PHA material having a vinyl-terminated side-chain from a vinyl-terminated fatty acid via a bacterial fermentation process;
   forming a PHA material having a hydroxyl-terminated side-chain from the PHA material having the vinyl-terminated side-chain; and
   chemically reacting the PHA material having the hydroxyl-terminated side-chain with 1,4-phenylenedimethanethiol to form a side-chain-functionalized PHA material having a side-chain with a terminal cross-linkable thiol group.

2. A process of forming a side-chain-functionalized polyhydroxyalkanoate (PHA) material, the process comprising:
   forming a PHA material having a vinyl-terminated side-chain from a vinyl-terminated fatty acid via a bacterial fermentation process;
   forming a PHA material having a hydroxyl-terminated side-chain from the PHA material having the vinyl-terminated side-chain; and
   chemically reacting the PHA material having the hydroxyl-terminated side-chain with a chlorocoumarin to form a side-chain-functionalized PHA material having a side-chain with a terminal cross-linkable coumarin group.

3. The process of claim 2, wherein the chlorocoumarin includes 6-chlorocoumarin.

4. A process of forming a side-chain-functionalized polyhydroxyalkanoate (PHA) material, the process comprising:
   forming a PHA material having a vinyl-terminated side-chain from a vinyl-terminated fatty acid via a bacterial fermentation process;
   forming a PHA material having a hydroxyl-terminated side-chain from the PHA material having the vinyl-terminated side-chain; and
   chemically reacting the PHA material having the hydroxyl-terminated side-chain with 2-furoyl chloride to form a side-chain-functionalized PHA material having a side-chain with a terminal cross-linkable furoyl group.

* * * * *